(12) United States Patent
Sivadas

(10) Patent No.: US 10,398,366 B2
(45) Date of Patent: Sep. 3, 2019

(54) RESPONDING TO CHANGES IN EMOTIONAL CONDITION OF A USER

(75) Inventor: Sunil Sivadas, Tampere (FI)

(73) Assignee: NOKIA TECHNOLOGIES OY, Espoo (FI)

(*) Notice: Subject to any disclaimer, the term of this patent is extended or adjusted under 35 U.S.C. 154(b) by 1023 days.

(21) Appl. No.: 12/829,122

(22) Filed: Jul. 1, 2010

(65) Prior Publication Data

US 2012/0004511 A1 Jan. 5, 2012

(51) Int. Cl.

| | |
|---|---|
| A61B 5/00 | (2006.01) |
| A61B 5/16 | (2006.01) |
| H04N 1/00 | (2006.01) |
| H04N 1/32 | (2006.01) |
| A61B 5/024 | (2006.01) |
| A61B 5/053 | (2006.01) |
| H04N 101/00 | (2006.01) |

(52) U.S. Cl.
CPC ......... *A61B 5/165* (2013.01); *H04N 1/00307* (2013.01); *H04N 1/00323* (2013.01); *H04N 1/32128* (2013.01); *A61B 5/024* (2013.01); *A61B 5/0533* (2013.01); *H04N 2101/00* (2013.01); *H04N 2201/0084* (2013.01); *H04N 2201/3266* (2013.01); *H04N 2201/3278* (2013.01)

(58) Field of Classification Search
CPC ....... A61B 5/165; A61B 5/024; A61B 5/0533; H04N 1/00307; H04N 1/00323; H04N 1/32128; H04N 2201/0084; H04N 2201/3266; H04N 2201/3278; H04N 2101/00
See application file for complete search history.

(56) References Cited

U.S. PATENT DOCUMENTS

| | | | |
|---|---|---|---|
| 5,367,454 A | 11/1994 | Kawamoto et al. | |
| 5,508,718 A | 4/1996 | Haikin | |
| 5,615,320 A | 3/1997 | Lavendel | |
| 5,722,418 A * | 3/1998 | Bro | 600/545 |
| 6,190,314 B1 | 2/2001 | Ark et al. | |
| 6,400,996 B1 | 6/2002 | Hoffberg et al. | |
| 6,466,232 B1 | 10/2002 | Newell et al. | |
| 6,505,167 B1 | 1/2003 | Horvitz et al. | |

(Continued)

FOREIGN PATENT DOCUMENTS

| | | |
|---|---|---|
| CN | 101087332 A | 12/2007 |
| EP | 1 509 042 A1 | 2/2005 |

(Continued)

OTHER PUBLICATIONS

International Search Report and Written Opinion for Application No. PCT/IB2011/052885 dated Oct. 19, 2011.

(Continued)

*Primary Examiner* — Michael W Kahelin
*Assistant Examiner* — Shirley Jian
(74) *Attorney, Agent, or Firm* — Alston & Bird LLP

(57) ABSTRACT

A method comprises monitoring inputs to a device from a user, using the user inputs to track an emotional condition of the user, detecting a change in the tracked emotional condition of the user, and in response to detecting the change, using a camera to capture an image of the user and inserting the image into a content item.

20 Claims, 2 Drawing Sheets

(56) References Cited

U.S. PATENT DOCUMENTS

| | | | |
|---|---|---|---|
| 6,585,521 B1* | 7/2003 | Obrador | G09B 23/28 369/27.01 |
| 6,963,839 B1* | 11/2005 | Ostermann | G10L 13/08 704/2 |
| 7,003,139 B2* | 2/2006 | Endrikhovski | G06F 3/011 382/118 |
| 7,181,693 B1 | 2/2007 | Anderson et al. | |
| 7,271,809 B2* | 9/2007 | Fedorovskaya | G06F 17/30244 345/581 |
| 7,280,041 B2* | 10/2007 | Ryou | G06F 3/011 128/903 |
| 7,327,505 B2* | 2/2008 | Fedorovskaya | G06F 3/011 358/527 |
| 7,484,175 B2* | 1/2009 | Kirkland | H04M 1/72555 715/751 |
| 7,607,097 B2* | 10/2009 | Janakiraman et al. | 715/753 |
| 7,853,863 B2* | 12/2010 | Sakai | 715/200 |
| 7,908,554 B1 | 3/2011 | Blattner | |
| 7,953,255 B2* | 5/2011 | Amento | G06T 13/40 382/118 |
| 7,970,716 B2* | 6/2011 | Shin | G06N 3/004 706/12 |
| 8,055,444 B2* | 11/2011 | Salay | G06F 3/0481 701/438 |
| 8,065,240 B2* | 11/2011 | Jung et al. | 706/2 |
| 8,154,615 B2* | 4/2012 | Fedorovskaya | G06Q 30/02 348/222.1 |
| 8,161,111 B2* | 4/2012 | Espelien | H04N 7/17318 345/156 |
| 8,239,774 B2 | 8/2012 | Gandhi et al. | |
| 8,285,085 B2 | 10/2012 | Manico et al. | |
| 8,435,115 B2* | 5/2013 | Walker | G07F 17/32 463/16 |
| 8,687,925 B2* | 4/2014 | Sano | A61B 5/16 382/160 |
| 8,694,899 B2* | 4/2014 | Goossens | G06Q 10/10 715/706 |
| 8,788,951 B2* | 7/2014 | Zalewski | A63F 13/31 345/473 |
| 8,913,004 B1 | 12/2014 | Bozarth et al. | |
| 9,900,498 B2* | 2/2018 | Kim | G06F 3/011 |
| 2002/0054086 A1 | 5/2002 | Van Oostenbrugge et al. | |
| 2002/0082007 A1* | 6/2002 | Hoisko | H04M 1/72544 455/412.1 |
| 2003/0110450 A1* | 6/2003 | Sakai | 715/529 |
| 2003/0179229 A1 | 9/2003 | Van Erlach et al. | |
| 2004/0059712 A1 | 3/2004 | Dean et al. | |
| 2004/0082839 A1* | 4/2004 | Haugen | 600/300 |
| 2004/0223605 A1* | 11/2004 | Donnelly | H04M 3/02 379/373.01 |
| 2005/0076051 A1 | 4/2005 | Carobus et al. | |
| 2005/0159958 A1* | 7/2005 | Yoshimura | 704/276 |
| 2005/0280545 A1* | 12/2005 | Ryou | G06F 3/011 340/573.1 |
| 2006/0170945 A1 | 8/2006 | Bill | |
| 2006/0177525 A1 | 8/2006 | Takagaki et al. | |
| 2006/0252455 A1* | 11/2006 | Van Stuivenberg | H04M 1/72547 455/556.1 |
| 2007/0288898 A1 | 12/2007 | Isberg | |
| 2008/0027984 A1 | 1/2008 | Perdomo et al. | |
| 2008/0077569 A1 | 3/2008 | Lee et al. | |
| 2008/0253695 A1* | 10/2008 | Sano | A61B 5/16 382/305 |
| 2009/0002178 A1 | 1/2009 | Shai et al. | |
| 2009/0024050 A1* | 1/2009 | Jung | A61B 5/16 600/544 |
| 2009/0055484 A1* | 2/2009 | Vuong | G06Q 10/107 709/206 |
| 2009/0110246 A1 | 4/2009 | Olsson et al. | |
| 2009/0112617 A1* | 4/2009 | Jung et al. | 705/2 |
| 2009/0112621 A1* | 4/2009 | Jung et al. | 705/2 |
| 2009/0177607 A1 | 7/2009 | Matsushima | |
| 2009/0313236 A1 | 12/2009 | Hernacki et al. | |
| 2010/0022279 A1* | 1/2010 | Hoberg | H04M 3/02 455/567 |
| 2010/0141662 A1* | 6/2010 | Storey | H04M 1/72544 345/473 |
| 2010/0223581 A1* | 9/2010 | Manolescu et al. | 715/853 |
| 2010/0240416 A1 | 9/2010 | Knight | |
| 2011/0040155 A1 | 2/2011 | Guzak et al. | |
| 2011/0093272 A1* | 4/2011 | Isobe | G10L 13/10 704/258 |
| 2011/0148916 A1 | 6/2011 | Blattner | |
| 2011/0191167 A1 | 8/2011 | Agarwal et al. | |
| 2012/0011477 A1 | 1/2012 | Sivadas | |
| 2012/0036080 A1 | 2/2012 | Singer et al. | |
| 2012/0059787 A1* | 3/2012 | Brown et al. | 706/52 |

FOREIGN PATENT DOCUMENTS

| | | |
|---|---|---|
| EP | 1 522 256 A1 | 4/2005 |
| EP | 1 523 160 A1 | 4/2005 |
| EP | 1 589 734 A2 | 10/2005 |
| GB | 2 400 667 A | 10/2004 |
| JP | 2004/199550 A | 7/2004 |
| JP | 2007/156776 A | 6/2007 |
| JP | 2008/108275 A | 5/2008 |
| JP | 2008/126954 A | 6/2008 |
| JP | 2009/141516 A | 6/2009 |
| KR | 2006/0102651 A | 9/2006 |
| KR | 2008/0057030 A | 6/2008 |
| WO | WO 2007/096706 A2 | 8/2007 |
| WO | WO 2007/141052 A1 | 12/2007 |
| WO | PCT/IB2010/050363 | 1/2010 |

OTHER PUBLICATIONS

Rubin, V.L., et al; 2004; "Discerning Emotions in Texts", The AAAI Symposium on Exploring Attitude and Affect in Text. AAAI-EAAT 2004. Stanford, CA; 4 pages.

Strapparava, C., et al; 2008; "Learning to identify emotions in text" In Proceedings of the 2008 ACM Symposium on Applied Computing (Fortaleza, Ceara, Brazil, Mar. 16-20, 2008). SAC '08. ACM, New York, NY; pp. 1556-1560.

Ikehara, C.S., et al; 2005; "Assessing Cognitive Load with Physiological Sensors", ISSN: 1530-1605, Print ISBN: 0-7695-2268-8; pp. 1-9.

Young, S; May 2010; "Cognitive User Interfaces" IEEE Signal Processing Magazine, 27(3): pp. 128-140.

Singh, V.; "Context-awareness: Control over disclosure and privacy in a social Environment", Networking laboratory, Helsinki University of Technology, TKK T-110.5190 Seminar on Internetworking Apr. 28-29, 2008; 7 pages.

Mori, J., et al; 2003; "Using Bio-signals to Track the Effects of a Character-based Interface"; 6 pages.

Felzer, T., et al; "How to Operate a PC Without Using the Hands", ASSETS'05, Oct. 9-12, 2005, Baltimore, Maryland, USA. ACM 1595931597/05/0010; pp. 198-199.

Warner, D., et al; 1994; bio-cybernetics a biologically responsive interactive interface: "Adventures in the Next Paradigm of Human Computer Interaction"; 4 pages.

Prendinger, H., et al; 2005; "The Empathic Companion: A Character-Based Interface That Addresses Users' Affective States", Applied Artificial Intelligence, 19; pp. 267-285, ISSN: 0883-9514 print/ 1087-6545 online, DOI: 10.1080/08839510590910174.

Nuttall, C., "Race to tap into real-time digital torrent", FT.Com, Apr. 12, 2009; [Retrieved on Oct. 19, 2010]; Retrieved from the Internet <URL: http://www.ft.com/cms/s/0/8c457976-278c-11de-9677-00144feabdc0.html; 2 pages.

Office Action for U.S. Appl. No. 12/834,403 dated Nov. 20, 2012.

International Search Report and Written Opinion for International Application No. PCT/IB2011/052963, dated Dec. 15, 2011.

Extended European Search Report from European Application No. 11800289.8, dated Aug. 30, 2013.

Final Office Action for U.S. Appl. No. 12/834,403 dated Nov. 20, 2012.

(56) References Cited

OTHER PUBLICATIONS

Final Office Action for U.S. Appl. No. 12/834,403 dated Jun. 18, 2014.
Final Office Action for U.S. Appl. No. 12/834,403 dated Mar. 26, 2015.
Office Action for U.S. Appl. No. 12/834,403 dated Aug. 2, 2012.
Office Action for U.S. Appl. No. 12/834,403 dated Feb. 13, 2014.
Office Action for U.S. Appl. No. 12/834,403 dated Dec. 3, 2014.
Office Action for European Application No. 11 800 289.8 dated Mar. 16, 2017.
Decision on Appeal for U.S. Appl. No. 12/834,403 dated Apr. 3, 2017.
Extended European Search Report from European Application No. 11806373.4, dated Mar. 7, 2016.
Khalili, Z. et al., *Emotion Detection Using Brain and Peripheral Signals*, Proceedings of the 2008 IEEE, CIBEC'08 (2008) 4 pages.
Office Action for European Application No. 11806373.4 dated Apr. 20, 2018, 6 pages.
Intention to Grant for European Application No. 11800289.8 dated Feb. 6, 2019, 6 pages.

* cited by examiner

RESPONDING TO CHANGES IN EMOTIONAL CONDITION OF A USER

FIELD OF THE INVENTION

This invention relates to responding to changes in a tracked emotional condition of a user.

BACKGROUND TO THE INVENTION

It is known to represent emotions in text-based messages, such as short message service (SMS) messages, emails, blogs and such like, using emoticons. These are constructed from two or more ASCII characters, and often represent a human face having a certain expression. Emoticons can be inserted into text by a user entering the relevant sequence of ASCII characters. With some mobile devices, emoticons can be selected from a menu and then inserted into text.

SUMMARY OF THE INVENTION

A first aspect of the invention provides a method comprising:
  monitoring inputs to a device from a user;
  using the user inputs to track an emotional condition of the user;
  detecting a change in the tracked emotional condition of the user; and
  in response to detecting the change, using a camera to capture an image of the user and inserting the image into a content item.

Detecting a change in the tracked emotional condition of the user may comprise determining that there has been a change in the emotional condition of the user.

The camera may be a front camera of the device.

The method may comprise communicating the content item from the device to a remote apparatus.

Using the user inputs to track an emotional condition of the user may comprise tracking a typing speed of the user and detecting a change in the tracked emotional condition of the user may comprise detecting a change in typing speed.

Using the user inputs to track an emotional condition of the user may comprise detecting a frequency of use of a backspace or delete function and detecting a change in the tracked emotional condition of the user may comprise detecting an increase in the frequency of use of a backspace or delete function.

Using the user inputs to track an emotional condition of the user may comprise monitoring a typing pressure of the user and detecting a change in the tracked emotional condition of the user may comprise detecting a change in average typing pressure. Detecting a change in the tracked emotional condition of the user may comprises determining that there has been a change in typing speed.

Using the user inputs to track an emotional condition of the user may comprise monitoring a physiological parameter of the user and detecting a change in the tracked emotional condition of the user may comprises detecting a change in the physiological parameter. Detecting a change in the tracked emotional condition of the user may comprises determining that there has been a change in the physiological parameter.

Using the user inputs to track an emotional condition of the user and to detect a change in the tracked emotional condition of the user may comprise detecting the typing by the user of plural characters that together constitute an emoticon. Detecting a change in the tracked emotional condition of the user may comprise determining that a user has typed plural characters that together constitute an emoticon.

A second aspect of the invention provides apparatus comprising
  at least one processor; and
  at least one memory including computer program code the at least one memory and the computer program code configured to, with the at least one processor, cause the apparatus at least to perform a method of:
  monitoring inputs to a device from a user;
  using the user inputs to track an emotional condition of the user;
  detecting a change in the tracked emotional condition of the user; and
  in response to detecting the change, using a camera to capture an image of the user and inserting the image into a content item.

Detecting a change in the tracked emotional condition of the user may comprise determining that there has been a change in the emotional condition of the user.

A third aspect of the invention provides apparatus comprising:
  means for monitoring inputs to a device from a user;
  means for using the user inputs to track an emotional condition of the user;
  means for detecting a change in the tracked emotional condition of the user; and
  means responsive to detecting the change for using a camera to capture an image of the user and inserting the image into a content item.

A fourth aspect of the invention provides apparatus comprising a processor, a memory and computer code stored in the memory and controlling operation of the processor, the apparatus comprising:
  computer code for monitoring inputs to a device from a user;
  computer code for using the user inputs to track an emotional condition of the user;
  computer code for detecting a change in the tracked emotional condition of the user; and
  computer code for being responsive to detecting the change to use a camera to capture an image of the user and to insert the image into a content item.

A fifth aspect of the invention provides a non-transitory computer readable medium having stored thereon instructions for causing computing apparatus to perform a method comprising:
  monitoring inputs to a device from a user;
  using the user inputs to track an emotional condition of the user;
  detecting a change in the tracked emotional condition of the user; and
  in response to detecting the change, using a camera to capture an image of the user and inserting the image into a content item.

A sixth aspect of the invention provides a computer program, optionally stored on a medium, comprising instructions for causing computer apparatus to perform a method as recited above.

BRIEF DESCRIPTION OF THE DRAWINGS

Embodiments of the present invention will now be described, by way of example only, with reference to the accompanying drawings, in which.

DETAILED DESCRIPTION OF EMBODIMENTS

Figure 1:
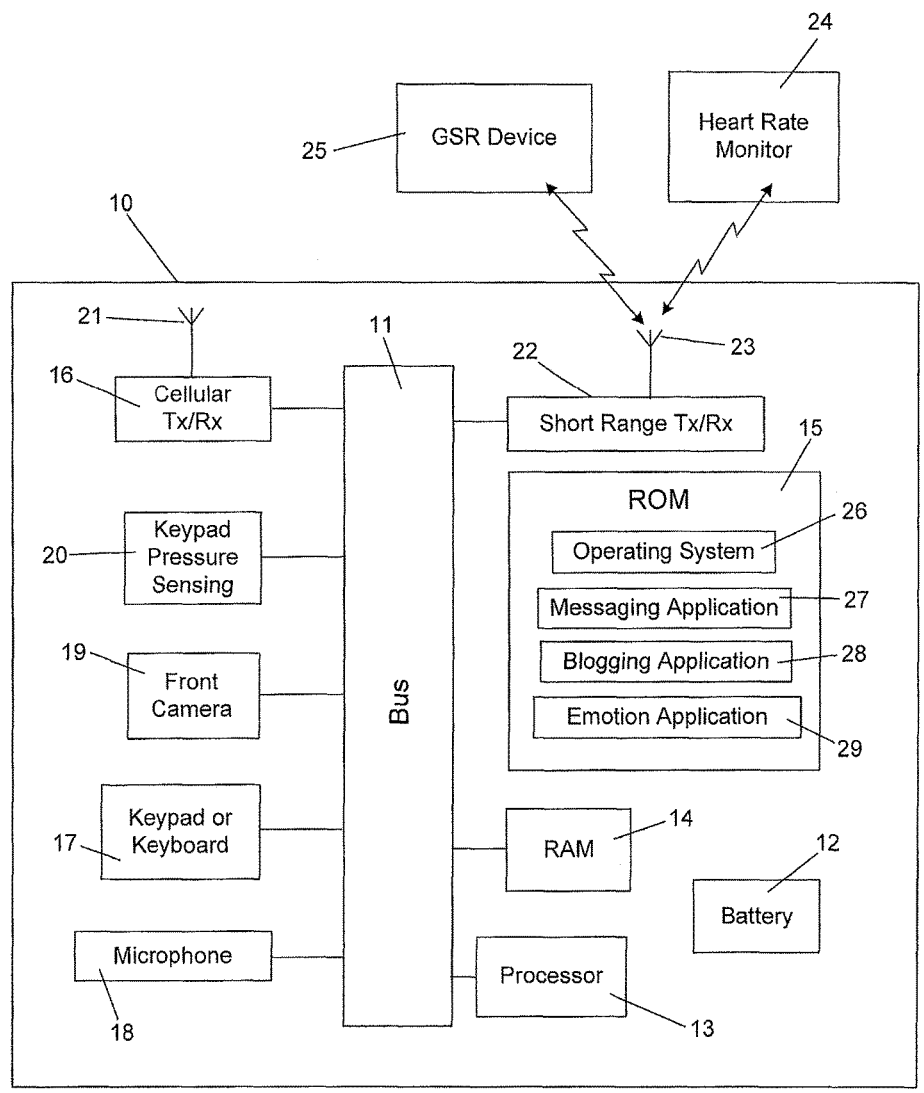
FIG. 1 is a schematic diagram illustrating a mobile device according to aspects of the invention.

Referring firstly to FIG. 1, a mobile device 10 includes a number of components. Each component is commonly connected to a system bus 11, with the exception of a battery 12. Connected to the bus 11 are a processor 13, random access memory (RAM) 14, read only memory (ROM) 15, a cellular transmitter and receiver (transceiver) 16 and a keypad or keyboard 17. The cellular transceiver 16 is operable to communicate with a mobile telephone network by way of an antenna 21

The keypad or keyboard 17 may be of the type including hardware keys, or it may be a virtual keypad or keyboard, for instance implemented on a touch screen. The keypad or keyboard provides means by which a user can enter text into the device 10. Also connected to the bus 11 is a microphone 18. The microphone 18 provides another means by which a user can communicate text into the device 10.

The device 10 also includes a front camera 19. This camera is a relatively low resolution camera that is mounted on a front face of the device 10. The front camera 19 might be used for video calls, for instance.

The device 10 also includes a keypad or keyboard pressure sensing arrangement 20. This may take any suitable form. The function of the keypad or keyboard pressure sensing arrangement 20 is to detect a pressure that is applied by a user on the keypad or keyboard 17 when entering text. The form may depend on the type of the keypad or keyboard 17.

The device includes a short range transceiver 22, which is connected to a short range antenna 23. The transceiver may take any suitable form, for instance it may be a Bluetooth transceiver, an IRDA transceiver or any other standard or proprietary protocol transceiver. Using the short range transceiver 22, the mobile device 10 can communicate with an external heart rate monitor 24 and also with an external galvanic skin response (GSR) device 25.

Within the ROM 15 are stored a number of computer programs and software modules. These include an operating system 26, which may for instance be the MeeGo operating system or a version of the Symbian operating system. Also stored in the ROM 15 are one or more messaging applications 27. These may include an email application, an instant messaging application and/or any other type of messaging application that is capable of accommodating a mixture of text and image(s). Also stored in the ROM 15 are one or more blogging applications 28. This may include an application for providing microblogs, such as those currently used for instance in the Twitter service. The blogging application or applications 28 may also allow blogging to social networking services, such as Facebook and the like. The blogging applications 28 allow the user to provide status updates and other information in such a way that it is available to be viewed by their friends and family, or by the general public, for instance through the Internet. In the following description, one messaging application 27 and one blogging application are described for simplicity of explanation.

Also stored in the ROM 15 is an emotion expressing software application 29, which is described in more detail below. The emotion expression application 29, briefly, is able to cause a photograph of the user's face, allowing a recipient to see expressions of emotion of the user, into a content item, for instance a text string being handled by one of the messaging applications 27 or by one of the blogging applications 28.

Although not shown in the Figure, the ROM 15 also includes various other software that together allow the device 10 to perform its required functions.

The device 10 may for instance be a mobile telephone or a smart phone. The device 10 may instead take a different form factor. For instance the device 10 may be a personal digital assistant (PDA), or netbook or similar. The device 10 preferably is a battery-powered handheld communications device.

The heart rate monitor 24 is configured to be supported by the user at a location such that it can detect the user's heartbeats. The GSR device 25 is worn by the user at a location where it is in contact with the user's skin, and as such is able to measure parameters such as resistance.

Figure 2:
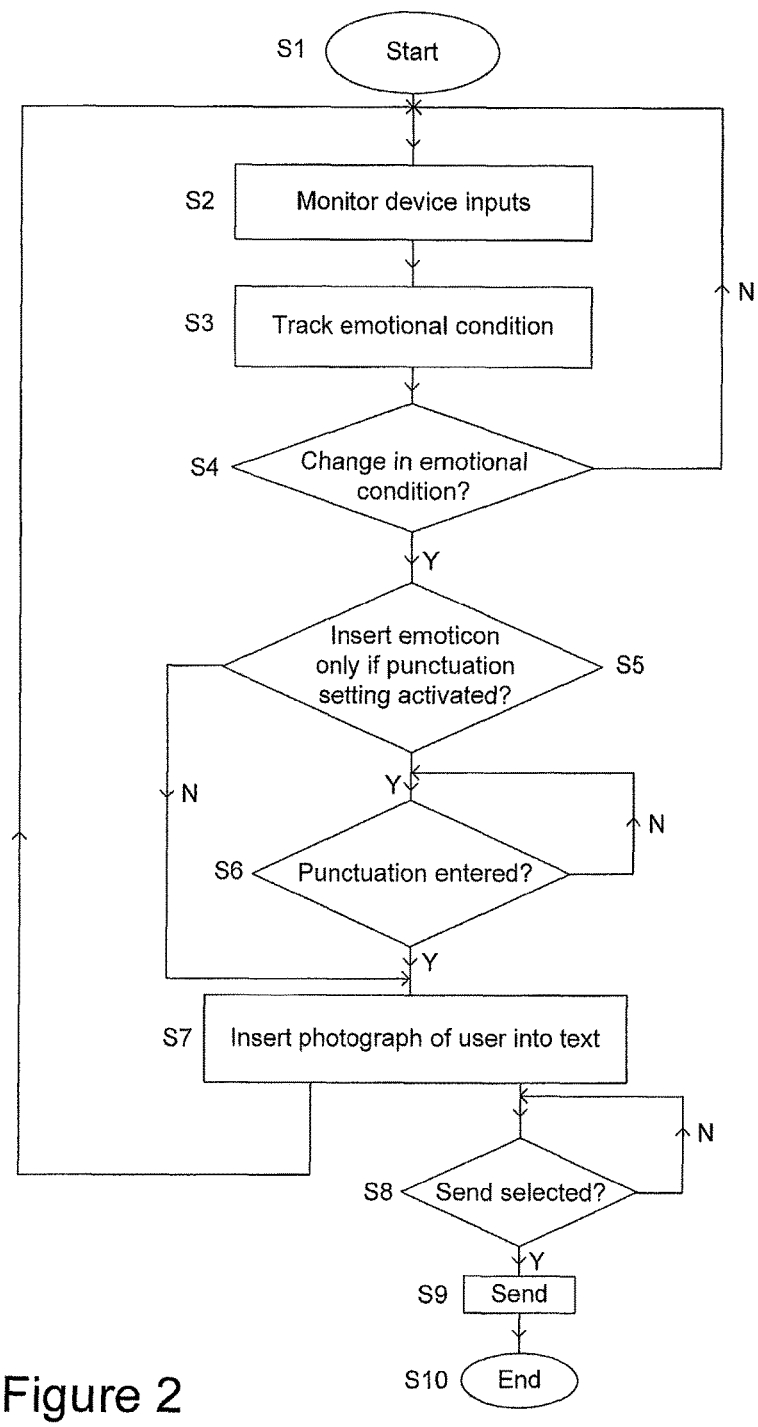
FIG. 2 is a flow chart illustrating operation of the FIG. 1 mobile device according to aspects of the invention.

Referring now to FIG. 2, operation of the emotion expression application 29 will now be described. The operation starts at step S1. Although not shown in FIG. 2, the emotion expression application 29 is active when either or both of the messaging application 27 and the blogging application 28 are in use by a user. The emotion expression application 29 is responsive upon detection that a user is entering text into the messaging application 27 or the blogging application 28 to monitor device inputs at step S2. It will be appreciated that text may be entered by the user either using the keypad or keyboard 17 or by dictating to the device through the microphone 18. In the latter case, voice recognition software (not shown) provides text to the messaging application 27 or the blogging application 28.

Step S2 involves the emotion expression application 29 monitoring signals and data provided by the keypad or keyboard 17, and in particular by monitoring a typing speed of the user. The emotion expression application 29 is configured to determine an average typing speed of the user, and to compare a current typing speed with the average speed. The current typing speed may be averaged over a period of time, for instance 10 seconds, optionally in a rolling window manner.

Step S2 alternatively or in addition comprises monitoring signals provided by the keypad or keyboard pressure sensing arrangement 20. The emotion expression application 29 is configured to monitor a pressure with which the user provides inputs on the keypad or keyboard 17. The emotion expression application 29 is configured to determine an average pressure, and to compare a current pressure with the average. The average may be determined over a predetermined time period or over a predetermined number of key presses, for instance.

Step S2 may alternatively or in addition involve monitoring information and signals received from the heart rate monitor 24. The emotion expression application 29 may be configured to detect the heart rate of the user by signals emanating from the heart rate monitor 24.

Step S2 may alternatively or in addition involve the emotion expression application 29 monitoring signals received from the GSR device 25. The emotion expression application 29 may determine a typical parameter value for the user, and from the typical parameter value be able to detect whether a current parameter is significantly above or significantly below the typical value.

At step S3, the emotion expression application 29 is configured to track the emotional condition of the user, using the device inputs that are monitored at step S2. Steps S2 and S3 may be performed in parallel, with step S2 in effect being performed continually.

Step S3 involves the emotion expression application 29 making a determination as to an emotional condition of the user, and updating the emotional condition periodically. The emotional condition may be updated frequently, for instance at intervals between half a second and 5 seconds, preferably at between intervals of between 1 second and 2 seconds. The emotional condition may be represented by the emotion expression application 29 in terms of a category. Example categories include normal, excited, happy, stressed, tired, upset etc. Alternatively, the emotional condition may take a numerical value.

At step S4, it is determined whether a change in the emotional condition of the user has occurred. If the emotion condition as tracked at step S3 has not changed significantly within a given time period, then step S4 yields a negative determination, and the operation proceeds again to step S2. If the emotional condition that is tracked in step S3 has changed by a significant degree, then step S4 yields a positive result, and operation progresses to step S5.

The details of step S4 depend on the nature of the device inputs that are being monitored to track the emotional condition at step S3. For instance, a change in emotional condition may be inferred when the emotion expression application 29 detects that the pressure applied on the keypad or keyboard by the user, as detected by the pressure sensing arrangement 20, differs from usual levels by an amount exceeding a threshold.

Alternatively or in addition, a change in emotional condition may be inferred when the emotion expression application 29 detects that a speed of typing by the user into the keypad or keyboard 17 deviates from the usual typing speed by more than a threshold.

For instance, an increase in typing speed by more than 20% may indicate that the user is in an excited condition.

A change in emotional condition may be inferred also when the emotion expression application 29 detects that a skin resistance parameter of the user, as measured by the GSR device 25, as fallen below a threshold or fallen by more than a predetermined amount. A decrease in skin resistance can indicate that the user is excited or stressed.

Detecting that the user is using a back space or delete key or keys of the keypad or keyboard 17 to an extent that is not usual for the user is used by the emotion expression application 29 to infer a change in emotional condition. For instance, an amount of use of backspace or delete keys that deviates from a typical amount to an extent that exceeds a threshold, the threshold perhaps being specific to the user, may indicate that the user is nervous, stressed or alternatively very excited.

A change in emotional condition may be inferred alternatively or additionally when the user's heart rate, as detected by the heart rate monitor 24, is determined by the emotion expression application 29 to have risen by an amount exceeding a threshold within a given time period. For instance, a change in emotional condition may be inferred when the user's heart rate increases by more than 10% within a period of less than 20 seconds. An increase in heart rate may indicate that the user is excited or frightened.

A change in emotional condition may be inferred alternatively by the user typing an emoticon. This can be inferred because it can be assumed that a user types an emoticon only when they wish to express an emotion, and because it can be assumed that this occurs only when there is a change in emotion. In this alternative, step S4 involves the emotion expression application detecting a sequence of key presses that result in ASCII characters that together constitute an emoticon.

Step S4 may comprise utilising inputs from a number of different sources. For instance, step S4 may involve cross-referencing information from the heart rate monitor 24 with information about the pressure of keypad or keyboard inputs from the keypad pressure sensing apparatus 20. In this way, the device 10 can more accurately determine an emotional condition of the user when utilising information from one source alone could provide an ambiguous result.

At step S5 it is determined whether a device setting that a photograph of the user's face is to be inserted into a message only at punctuation points is positive or negative. The setting is able to be changed by a user, and has a default setting. If the setting is positive, the operation proceeds to step S6. Here, it is determined whether punctuation has been entered by the user. In the event of a negative determination, the operation returns again to step S6. In the event of a negative determination from step S6 or a negative determination from step S5, the operation proceeds to step S7. Step S6 may exclude detecting punctuation that forms an emoticon.

At step S7, the emotion expression application 29 inserts a photograph of the user into the text string that is being entered by the user into the messaging application 27 or the blogging application 28. The image taken using the front camera is scaled to an appropriate size and may also be transformed to a colour map preferred by the user. Scaling the photograph may involve the emotion expression application 29 adjusting a size of the image provided by the front camera to a size suitable for inclusion into the text string. The size may be small, for instance approximately the size of an icon. The required size may be different depending on whether the image is being inserted into a text string of the blogging application 28 or the messaging application 27. The required size may vary depending on the type of the messaging application 27. The required size may be set by a user through a menu system of the device 10. Scaling may also involve changing other parameters of the image, for instance in order to reduce the amount of data that is needed to represent the image.

Following step S7, the operation proceeds again to step S2. In this way, changes in emotional conditions can result in further images being introduced into the text.

In parallel with steps S2 to S7, the operation determines at step S8 whether the user has selected a send or upload option of the messaging application 27 or the blogging application 28. In the event of a positive determination, the message is sent or the blog uploaded at step S9. Step S9 involves the messaging application 27 or the blogging application 28 and the transceiver 16. Following step S9, the operation ends at step S10.

It will be appreciated that steps and operations described above are performed by the processor 13, using the RAM 14, under control of instructions that form part of the emotion expression application 29 and/or the messaging application 27 or the blogging application 28, running on the operating system 26. During execution, some or all of the computer program that constitutes the operating system 26, the messaging application 27, the blogging application 28 and the emotion expression application 29 may be stored in the RAM 14. In the event that only some of this computer program is stored in the RAM 14, the remainder resides in the ROM 15.

It should be realized that the foregoing embodiments should not be construed as limiting. Other variations and modifications will be apparent to persons skilled in the art upon reading the present application.

Moreover, the disclosure of the present application should be understood to include any novel features or any novel combination of features either explicitly or implicitly disclosed herein or any generalization thereof and during the prosecution of the present application or of any application derived therefrom, new claims may be formulated to cover any such features and/or combination of such features.

What is claimed is:

1. A method comprising:
   monitoring, by a processor, device inputs to a messaging application of a device, wherein the device inputs are from a user and create a content item of a message;
   using, by the processor, the device inputs to track an emotional condition of the user by making a determination as to an emotional condition of the user, and updating the emotional condition of the user periodically;
   determining by the processor whether a change in the tracked emotional condition of the user has occurred within a given time period based, at least in part, on the monitored device inputs;
   in response to the processor determining that a change has occurred based, at least in part, on the monitored device inputs, causing the processor operably coupled to at least one memory, to control a camera to capture a photograph of the user such that the photograph is stored in the at least one memory, and inserting, by the processor, the photograph into the content item of the message; and
   in response to the processor determining that a change has not occurred continuing to monitor device inputs without causing the camera to capture a photograph and store a photograph in at least one memory.

2. The method as claimed in claim 1, comprising causing, by the processor, transmission of the content item of the message from the device to a remote apparatus.

3. The method as claimed in claim 1, wherein using, by the processor, the device inputs to track an emotional condition of the user comprises tracking a typing speed of the user and wherein detecting, by the processor, a change in the tracked emotional condition of the user comprises detecting a change in typing speed.

4. The method as claimed in claim 1, wherein using, by the processor, the device inputs to track an emotional condition of the user comprises monitoring a typing pressure of the user and wherein detecting, by the processor, a change in the tracked emotional condition of the user comprises detecting a change in average typing pressure.

5. The method as claimed in claim 1, further comprising monitoring, by the processor, a physiological parameter of the user and wherein determining, by the processor, the change in the tracked emotional condition of the user further comprises detecting, by a processor, a change in the at least one physiological parameter.

6. A method as claimed in claim 1 wherein determining, by the processor, whether a change in the tracked emotional condition has occurred comprises monitoring inputs from a plurality of different sources.

7. A method as in claim 6, wherein monitoring inputs from a plurality of different sources comprises said monitoring device inputs, and monitoring, by the processor, at least one physiological parameter.

8. A method as claimed in claim 7, wherein monitoring, by the processor, the at least one physiological parameter comprises monitoring signals received by the processor from at least one of a heart rate monitor or a galvanic skin response device.

9. A method as claimed in claim 1, wherein monitoring, by the processor, device inputs to a device comprises monitoring device inputs to the content item.

10. A method as claimed in claim 1, comprising determining by the processor whether punctuation has been entered into the content item and inserting by the processor the image of the user into the content item if the determination is positive.

11. The apparatus as claimed in claim 1, wherein using, by the processor, the device inputs to track an emotional condition of the user comprises detecting a frequency of use of a backspace or delete function and wherein detecting, by the processor, a change in the tracked emotional condition of the user comprises detecting an increase in the frequency of use of a backspace or delete function.

12. An apparatus comprising:
    at least one processor; and
    at least one memory including computer program code;
    the at least one memory and the computer program code configured to, with the at least one processor, cause the apparatus at least to perform a method of:
    monitoring device inputs to a messaging application of the apparatus,
    wherein the device inputs are from a
    user and create a content item of a message;
    using the device inputs to track an emotional condition of the user by making a determination as to an emotional condition of the user, and updating the emotional condition of the user periodically;
    determining whether a change in the tracked emotional condition of the user has occurred within a given time period based, at least in part, on the monitored device inputs;
    in response to determining that a change has occurred based, at least in part, on the monitored device inputs, causing a camera to capture a photograph of the user such that the photograph is stored in at least one memory and inserting the photograph into the content item of the message; and
    in response to determining that a change has not occurred, continuing to monitor device inputs without causing the camera to capture a photograph and store a photograph in at least one memory.

13. The apparatus as claimed in claim 12, wherein the camera is a front camera forming part of the apparatus.

14. The apparatus as claimed in claim 12, in which the computer readable instructions when executed by the at least one processor cause it to communicate the content item of the message from the device to a remote apparatus.

15. The apparatus as claimed in claim 12, wherein the computer readable instructions are configured to control the at least one processor to use the device inputs to track an emotional condition of the user by tracking a typing speed of the user and to detect a change in the tracked emotional condition of the user by detecting a change in typing speed.

16. The apparatus as claimed in claim 12, wherein the computer readable instructions are configured to control the at least one processor to use the device inputs to track an emotional condition of the user by detecting a frequency of use of a backspace or delete function and to detect a change in the tracked emotional condition of the user by detecting an increase in the frequency of use of a backspace or delete function.

17. The apparatus as claimed in claim 12, wherein the computer readable instructions are configured to control the at least one processor to use the device inputs to track an emotional condition of the user by monitoring a typing pressure of the user and to detect a change in the tracked emotional condition of the user by detecting a change in average typing pressure.

18. The apparatus as claimed in claim 12, wherein the computer readable instructions are configured to monitor at least one physiological parameter of the user and to detect a change in the tracked emotional condition of the user by detecting a change in the at least one physiological parameter.

19. A mobile device comprising the apparatus of claim 12.

20. A non-transitory computer readable medium having stored thereon instructions for causing computing apparatus to perform a method comprising:

monitoring device inputs to a messaging application of the apparatus, wherein the device inputs are from a user and create a content item of a message;

using the device inputs to track an emotional condition of the user by making a determination as to an emotional condition of the user, and updating the emotional condition of the user periodically;

determining whether a change in the tracked emotional condition of the user has occurred within a given time period based, at least in part, on the monitored device inputs;

in response to determining that a change has occurred based, at least in part, on the monitored device inputs, causing a camera to capture a photograph of the user such that the photograph is stored in at least one memory and inserting the photograph into the content item of the message; and in response to determining that a change has not occurred, continuing to monitor device inputs without causing the camera to capture a photograph and store a photograph in at least one memory.

\* \* \* \* \*